(12) United States Patent
Akiba et al.

(10) Patent No.: US 8,790,726 B2
(45) Date of Patent: Jul. 29, 2014

(54) DEODORANT AGENT

(75) Inventors: Syunichi Akiba, Tochigi (JP); Katsutoshi Ara, Tochigi (JP); Hiroshi Kusuoku, Tochigi (JP); Toyoki Hagura, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/548,998

(22) Filed: Aug. 27, 2009

(65) Prior Publication Data

US 2009/0317346 A1 Dec. 24, 2009

Related U.S. Application Data

(62) Division of application No. 10/550,858, filed as application No. PCT/JP03/11982 on Sep. 19, 2003, now abandoned.

(30) Foreign Application Priority Data

Apr. 7, 2003 (JP) ................................. 2003-103171

(51) Int. Cl.
*A61K 36/756* (2006.01)

(52) U.S. Cl.
USPC .............................. 424/769; 424/775; 424/65

(58) Field of Classification Search
None
See application file for complete search history.

(56) References Cited

U.S. PATENT DOCUMENTS

| | | | |
|---|---|---|---|
| 5,244,662 A | 9/1993 | Han et al. | |
| 5,344,648 A | 9/1994 | Haga et al. | |
| 6,319,523 B1 | 11/2001 | Zhou | |
| 6,548,088 B1 * | 4/2003 | Chen | 424/728 |
| 6,551,625 B1 | 4/2003 | Hilaire et al. | |
| 7,501,136 B2 | 3/2009 | Hagura et al. | |
| 2004/0047833 A1 | 3/2004 | Ishino et al. | |
| 2005/0100520 A1 | 5/2005 | Hagura et al. | |

FOREIGN PATENT DOCUMENTS

| | | |
|---|---|---|
| CN | 1076622 A | 9/1993 |
| CN | 1086724 * | 5/1994 |
| CN | 1127905 | 7/1996 |
| CN | 1 202 366 | 6/1997 |
| CN | 1 253 770 | 11/1998 |
| CN | 1 206 740 | 7/2002 |
| EP | 1 064 932 | 6/2000 |
| JP | 61-103447 | 5/1986 |
| JP | 01 016713 | 7/1989 |
| JP | 02-031648 | 2/1990 |
| JP | 3-109072 | 5/1991 |
| JP | JO 07-171210 | 7/1995 |
| JP | 10-158137 | 6/1998 |
| JP | 2000-44419 | 2/2000 |
| JP | 2001-64141 | 3/2001 |
| JP | 2001-64191 | 3/2001 |
| JP | 2002-003353 | 1/2002 |
| JP | 2002-29954 | 1/2002 |
| JP | 2002-212085 | 7/2002 |
| JP | 2002-212877 | 7/2002 |
| JP | 2002-226386 | 8/2002 |
| JP | 2002-255776 | 9/2002 |
| JP | 2003-113013 | 4/2003 |
| JP | 2003-292427 | 10/2003 |
| WO | WO 01/99376 | 12/2001 |
| WO | WO 02/51374 A1 | 7/2002 |
| WO | WO 02/83158 | 10/2002 |

OTHER PUBLICATIONS

Kunitomo (Yakugaku Zasshi (1962), vol. 82, pp. 611-13).*
English translation of Ishino-WO 02/051374; Jul. 2002.*
A Guide to Dermatohistopathology: 2$^{nd}$ Ed., pp. 29 and 528, by Appleton-Century-Crofts, New York, 1976.
Zenq et al, Proc. Natl. Acad. Sci. USA, 1966, vol. 93, pp. 6626-6630.
A Guide to Dermatohistopathology, 2$^{nd}$ Ed., pp. 29 and 528, by Appleton-Crofts, New York, 1978.
Zeng, et al., Proc. Natl. Acad. Sci. USA, 1966, vol. 93, pp. 6626-6630.
Takeuchi et al. (Igaku to Seibutsugaku (1994), vol. 128, No. 3, pp. 121-6.

* cited by examiner

*Primary Examiner* — Susan Hoffman
(74) *Attorney, Agent, or Firm* — Oblon, Spivak, McClelland, Maier & Neustadt, L.L.P.

(57) ABSTRACT

Deodorant agents, which contain *ginkgo* or *Phellodendron* Bark or its extract as an active ingredient and which are high in safety and can radically inhibit the emission of human body malodors typified by sweat odor, especially, axillary odor.

14 Claims, 2 Drawing Sheets

DEODORANT AGENT

FIELD OF THE INVENTION

This invention relates to deodorant agents, which inhibit the emission of human body malodors.

BACKGROUND OF THE INVENTION

Body odors are given off from all over the body, led by sweat odor, (and including) bad breath, scalp odor, foot odor and the like. Concerning sweat odor among these odors, it is composed of an axillary odor typified by "hircismus" and an acid odor emitted from all over the body. In recent years, there is an increasing desire for the control of an axillary odor as a typical example of odor that causes feeling of disgust.

In contrast to eccrine sweat glands, apocrine glands from which sweat is secreted as a source of an axillary odor are abundantly found at the axillae, the areolae, the pubes and the like. They are not found spreading widely and localized in these areas (for example, Pinkus H.; Mehregan A. H.; Adnexal Nevi and Benign Adnexoid Tumors, in A Guide to Dermatohistopathlogy; 2nd ed., pp 528, pp 29, by Appleton-Century-Crofts, New York, 1976). In recent years with an increasing inclination toward cleanliness, a need continues to exist for the persistent elimination of such an axillary odor.

It has been reported in recent years that 3-methyl-2-hexenoic acid (3M2H) is a key odor molecule of apocrine sweat. This is secreted from apocrine glands in covered form by apolipoprotein D On the skin surface, this protein is decomposed by resident skin flora existing, and hence, an odor is generated (for example, Zeng C., et al., Proc. Natl. Acad. Sci. U.S.A., 93, 6626-6630, 1996).

There are conventionally-known control techniques for human body malodors. First, sweat control techniques on antiperspiratory effects such as zinc paraphenolsulfonate, citric acid, and various aluminum and zirconium salts. Secondly, growth control techniques against causative microorganisms of human body malodors by antimicrobial agents such as triclosan and benzalkonium chloride. Thirdly, techniques for converting lower fatty acids, causative substances of body odors, into metal salts with zinc white (zinc oxide) or the like or deodorizing produced body malodors with substances having deodorizing effects such as flavonoid and chlorophyll. Finally, masking techniques by—fragrances of perfumes or colognes.

However,—these techniques are not sufficient for reducing body malodors led by axillary odor. Additionally, antimicrobial techniques may have a potential danger of a reduction in the primary barrier function of the skin, because they also destroy resident skin flora On the other hand, *ginkgo* has blood flow promoting effects and anti-inflammatory effects, and *Phellodendron* Bark has anti-inflammatory effects and intestinal function regulating effects. They are hence contained in Chinese herbal remedies, beverages and the like. It is, however, not known at all that they have an effect to inhibit body malodors.

An object of the present invention is to provide a deodorant agent which is high in safety and can radically inhibit the occurrence of human body malodors led by sweat odor, especially, axillary odor.

DISCLOSURE OF THE INVENTION

The present inventors were interested in the apocrine odor which is considered to be one of causative substances of human body malodors, and have proceeded with an investigation about inhibition of its formation. As a result, it has been found that certain particular plant extracts have an effect to inhibit the decomposition of apolipoprotein D, a carrier protein for odor molecules, by microorganisms resulting in reduction of malodors, and are useful substances capable of inhibiting the human body malodors.

Specifically, the present invention provides a deodorant agent comprising, as an active ingredient, *ginkgo* or *Phellodendron* Bark or an extract thereof.

The present invention also provides use of *ginkgo* or *Phellodendron* Bark or an extract thereof for the production of a deodorant agent.

The present invention further provides a method for inhibiting a body malodor, which includes applying *ginkgo* or *Phellodendron* Bark or an extract thereof to the skin.

MODES FOR CARRYING OUT THE INVENTION

Figure 1:
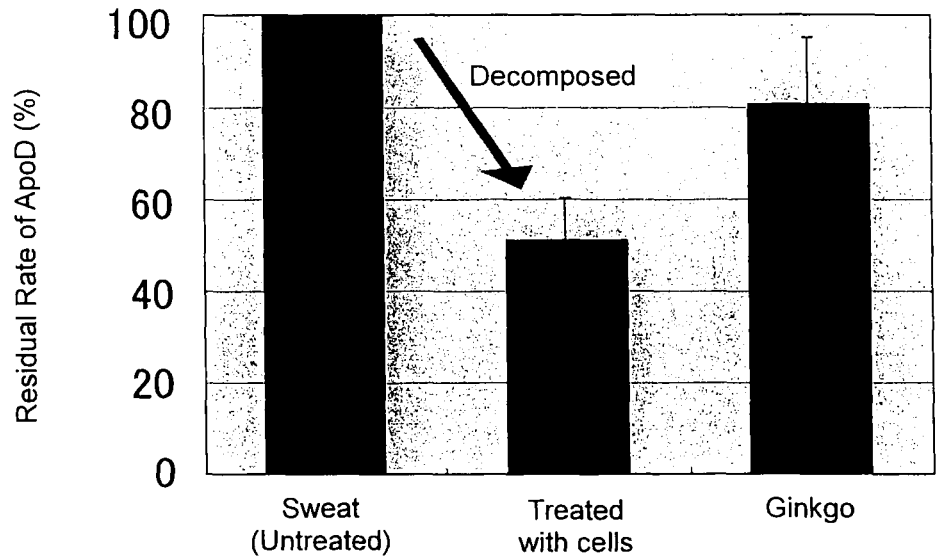
FIG. 1 is a diagram showing decomposition-inhibiting effects of a *ginkgo* extract for apolipoprotein D.

*Ginkgo* that can be used as a deodorant agent according to the present invention means *Ginkgo biloba* L. of the Ginkgoaceae family, whereas *Phellodendron* Bark that can be used as a deodorant agent according to the present invention means *Phellodendron amurens* Ruprecht of the Rutaceae family. As *ginkgo*, its leaves can be used either without modification or after grinding, with the use of leaves being preferred. As for *Phellodendron* Bark, on the other hand, the use of its bark is preferred.

The term "extract of *ginkgo* or *Phellodendron* Bark" as used herein means an extract in one of various solvents—which is obtained, for example, by extracting *ginkgo* leaves or *Phellodendron* Bark at room temperature or elevated temperature or extracting the same with an extraction apparatus such as Soxhlet extractor—its dilution, its concentrate, or its dried powder. The extract can be a mixed extract obtained from two or more plants.

Examples of the solvent usable for extraction include water; alcohols such as methanol, ethanol, propanol and butanol; ketones such as acetone, methyl ethyl ketone; esters such as methyl acetate and ethyl acetate; linear and cyclic ethers such as tetrahydrofuran and diethyl ether; halogenated hydrocarbons such as dichloromethane, chloroform and carbon tetrachloride; hydrocarbons such as hexane, cyclohexane and petroleum ether; aromatic hydrocarbons such as benzene and toluene; polyethers such as polyethylene glycol; pyridines; oils and fats, such as soybean oil, rapeseed oil, squalane, isopropyl myristate, palmitic acid, oleic acid, and linoleic acid; and supercritical carbon dioxide. They can be used either singly or in combination.

When used singly, low-polarity solvents such as ethanol, acetone, hexane, oils or fats, and supercritical carbon dioxide are preferred. When used in combination, on the other hand, water-alcohol mixed solvents are preferred, with a water-ethanol mixed solvent being more preferred. The content of ethanol can be preferably 50 v/v % or higher, more preferably 80 v/v % or higher, still more preferably 95 v/v % or higher.

Extraction conditions differ depending on the solvent to be used. When extracting with a water-ethanol mixed solvent, for example, it is preferred to use from 70 to 100 mL of the solvent per 10 of *ginkgo* or *phellodendron* bark and to conduct the extraction at a temperature of from 15 to 35° C., preferably from 20 to 25° C. for 30 hours to 10 days, preferably for 5 to 8 days.

The extract can be used after removing inert impurities from it by a technique such as liquid-liquid partition, and the use of such an extract is preferred in the present invention. They can also be used after subjecting them to treatment such as deodorizing and/or decoloring as needed by method(s) known per se in the art.

The *ginkgo* or *Phellodendron* Bark extract can be used without modification as a deodorant agent according to the present invention. As an alternative, the extract can also be used by diluting it or by concentrating or lyophilizing it and then preparing the concentrate or lyophilizate into a powder or paste-like form.

*Ginkgo* or *Phellodendron* Bark or an extract thereof as described above inhibits the decomposition of apolipoprotein D by microorganisms and inhibits the emission of body odors as will be demonstrated subsequently in examples. It is considered that causative substances (odor molecules) of human body odors, primarily the apocrine odor which is a causative odor of axillary odor are considered to be branched, unsaturated lower fatty acids typified by 3-methyl-2-hexenoic acid (3M2H), and also that such odor molecules are included in carrier proteins and secreted into sweat by apocrine glands and the carrier proteins are then decomposed and liberated by microorganisms residing on the skin (Zeng C., et al., Proc. Natl. Acad. Sci. U.S.A., 93, 6626-6630, 1996). As apolipoprotein D is a carrier protein for the odor molecules, it is considered to be possible to inhibit the production of body odors if such decomposition of apolipoprotein D can be inhibited.

Accordingly, the production of body odors can be inhibited by applying *ginkgo, Phellodendron* Bark or an extract thereof to the skin in accordance with the present invention, and a preparation with *ginkgo, Phellodendron* Bark or an extract thereof contained in an effective amount therein can serve as a deodorant agent which could eradicate the production of such causative substances of odors.

The deodorant agent according to the present invention can be used as preparations such as cosmetics, external drug products and quasi-drug products, for example, creams, emulsions, lotions, powders, sprays, sticks, sheets, and plasters such as poultices. It is also possible to use two or more application methods in combination.

Concerning the content of *ginkgo, Phellodendron* Bark or an extract thereof upon using the deodorant agent according to the present invention as a cosmetic, external drug product or quasi-drug product, the content of *ginkgo* or *Phellodendron* Bark can be set preferably at from 0.1 to 20 wt % in terms of dry weight basis in the composition, with from 0.5 to 10 wt % being preferred, and the content of the *ginkgo* or *Phellodendron* Bark extract can be set preferably at from 0.00001 to 10 wt % in terms of solid content basis in general, with from 0.0005 to 5 wt % being preferred.

In addition to various ingredients commonly employed in these cosmetics, external drug products or quasi-drug products, for example, those generally used as cosmetic ingredients such as oils, surfactants, alcohols, chelating agents, pH adjusters, preservatives, viscosity increasing agents, colorants and fragrances, other ingredients such as ultraviolet absorbers, whitening agents, anti-wrinkle agents, humectants, sebum excretion inhibitors, emollients, keratin protecting agents, pharmaceutically-active agents, antioxidants and solvents can be added in a desired combination upon preparation.

Moreover, the above-described preparations can each be provided with enhanced deodorant effects by adding finely-divided powder of a natural or synthesized, porous metal oxide, an astringent compound including a metal such as aluminum, zirconium or zinc as a component, a bactericidal agent, an antimicrobial agent, an antibiotic and/or the like as needed.

The deodorant agent according to the present invention can control the production of body odors by applying it to areas where malodors tend to occur, such as the feet, axillae, head and pubes. In such applications, the preparation can preferably be applied, for example, in an amount of from 1 to 20 mg in the case of a liquid preparation or in an amount of from 1 to 50 mg in the case of a solid preparation, per $cm^2$ of the skin, although it differs depending on the content of the active ingredient.

EXAMPLES

Production Example 1

Preparation of *Ginkgo* Extract

To leaves (10 g) of *ginkgo* (*Ginkgo biloba* L.), a 95 v/v % aqueous ethanol solution (85 mL) was added. Subsequent to extraction at room temperature for 7 days, filtration was conducted to obtain an extract (yield: 85 mL, evaporation residue: 1.59 w/v %).

Production Example 2

Preparation of *Phellodendron* Bark Extract

To bark (10 g) of *Phellodendron* Bark (*Phellodendron amurens* Ruprecht), a 95 v/v % aqueous ethanol solution (85 mL) was added. Subsequent to extraction at room temperature for 7 days, filtration was conducted to obtain an extract (yield: 85 mL, evaporation residue: 0.72 w/v %).

Example 1

Decomposition Inhibiting Effects for Apolipoprotein D (1) Preparation of Sweat

Absorbent cotton pads, each of which had been moistened with distilled water (1.5 mL), were held in the armpits of plural male subjects, the armpits having had the apocrine odor, and were then squeezed to collect a solution (57.5 mL). After the solution was filtered through a 0.45-μm filter, it was concentrated by "Centriprep YM-10" (Millipor Corporation). Distilled water was added again, and concentration was likewise conducted by "Centriprep YM-10" to remove low molecular weight substances. The thus-prepared solution was provided as a sweat concentrate.

Figure 3:
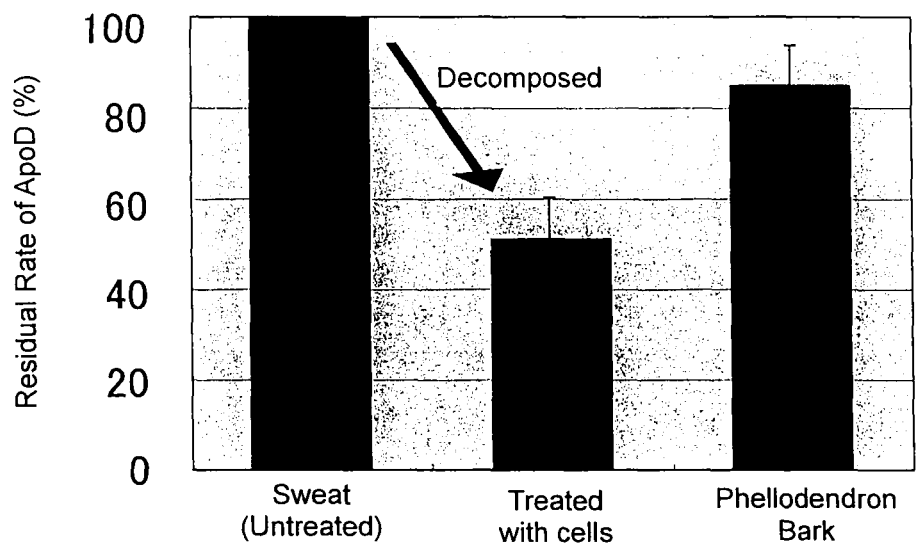
FIG. 3 is a diagram showing decomposition-inhibiting effects of a *Phellodendron* Bark extract for apolipoprotein D.

(2) To the sweat concentrate (0.04 mL) prepared by the above-described procedure (1), 100 mL Tris-HCl buffer (0.03 mL), distilled water (0.02 mL) and the *ginkgo* or *Phellodendron* Bark extract (0.1 mL) prepared in Preparation Example 1 and 2 were added. *Brevibacterium epiderumidis* which had been washed (three times) with 20 mL Tris-HCl buffer (pH 7.2) was inoculated to give a final cell count of about $10^8$ cfu/mL, and subsequent to incubation at 37° C. for 24 hours, antibody staining was performed. Sodium dodecyl sulfate polyacrylamide electrophoresis (SDS-PAGE) of the cell-treated sweat concentrate employed "Ready gel J" (separating gel concentration: 15%, Bio-Rad Laboratories, Inc.). As the antibody staining, proteins separated by the SDS-PAGE were electrically transferred from the gel onto a PVDF filter (Millipor Corporation, "Immobilon Transfer Membrane"), and apolipoprotein D was detected by "ECL Plus Western Blotting Detection System" (Amersham Pharmacia Biotech) while using an anti-apolipoprotein D monoclonal mouse antibody (RDI) as a primary antibody and an HRP-labeled anti-mouse Ig antibody (Amersham Pharmacia Biotech) as a secondary antibody, and image processing was performed, and then, the residual rate of apolipoprotein D (=the amount of apolipoprotein D in the sample/the amount of apolipoprotein D in the untreated sweat concentrate×100) was calculated. The results are shown in FIG. 1 and FIG. 3 (in the diagrams, "ApoD" stands for apolipoprotein D).

By the *Brevibacterium epiderumidis* treatment of the sweat concentrate, the apolipoprotein D in the sweat concentrate was decomposed and decreased. By the addition of the *ginkgo* extract or *Phellodendron* Bark extract, however, the decomposition of apolipoprotein D was inhibited.

Example 2

Body Odor Inhibition Test (1)

Figure 2:
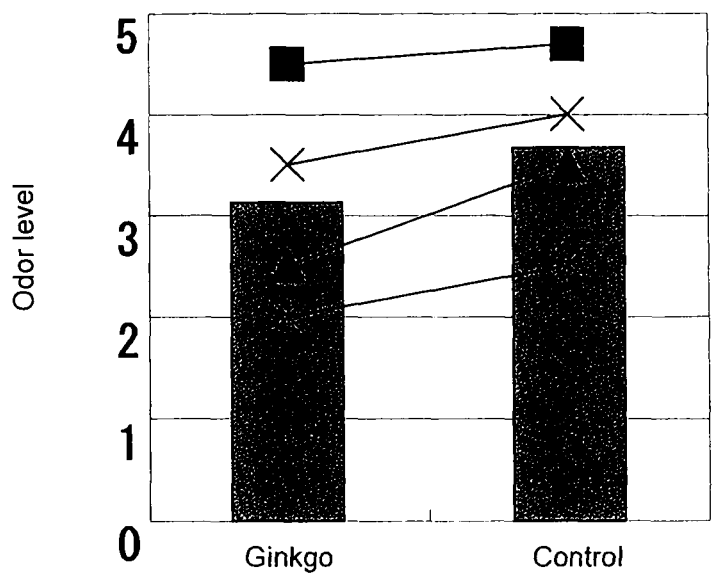
FIG. 2 is a diagram showing body-odor-inhibiting effects of the *ginkgo* extract.

A solution, which had been prepared by diluting the *ginkgo* extract to 10% concentration with 20% ethanol, was applied to one axillae of four subjects, and a control (20% ethanol, 0.5 g) was applied to the other axillae of the subjects, and axillary pads were worn in their both axillae. After seven hours, they entered an air-conditioned room of 40° C. and 75% RH and stayed there for 5 minutes. After eight hours, the axillary pads were collected, and an olfactory assessment was performed by a panel of three experts in accordance with the following standards, and the odor level was determined by an average of their scores. The results are shown in FIG. 2.

| | |
|---|---|
| 5: | very strong odor |
| 4: | strong odor |
| 3: | moderate odor |
| 2: | perceivable odor |
| 1: | weak odor |
| 0: | no odor |

By the application of the 10% *ginkgo* extract, the level of axillary odor of each subject was lowered, and the production of body odors was inhibited.

Example 3

Body Odor Inhibition Test (2)

Figure 4:
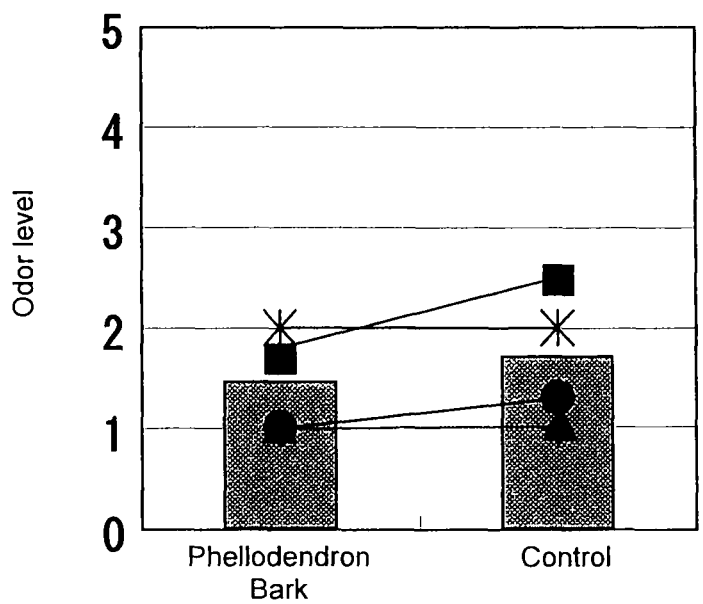
FIG. 4 is a diagram showing body-odor-inhibiting effects of the *Phellodendron* Bark extract.

The *Phellodendron* Bark extract prepared in Production Example 2 was concentrated to dryness, and then added to the ingredients shown below in Table 1 to give a solid content of 0.2%. Subsequently, a deodorant agent (stick) was prepared. By a similar method as in Example 2, its body odor inhibition effects were assessed. The results are shown in FIG. 4.

TABLE 1

| <Stick> | |
|---|---|
| Ingredients | % w/w |
| Aluminum zirconium tetrachlorohydrate glycine | 24.0 |
| Cyclomethicone | 54.8 |
| Stearyl alcohol | 15.0 |
| Hydrogenated castor oil | 5.0 |
| Silica | 1.0 |
| Phellodendron Bark extract | 0.2 |
| Total | 100.0 |

By the application of the 0.2% *Phellodendron* Bark extract, the level of axillary odor of each subject was lowered, and the production of body odors was inhibited.

INDUSTRIAL APPLICABILITY

The deodorant agent according to the present invention can persistently inhibit the emission of human body malodors, and therefore, is useful as a material having excellent deodorizing effects and high safety.

The invention claimed is:

1. A method for inhibiting a body odor, which comprises applying a deodorant agent comprising *Phellodendron* Bark extract obtained with 95 v/v % or higher aqueous ethanol solution to skin in need thereof.

2. The method of claim 1, wherein said *Phellodendron* Bark extract is obtained using 70 to 100 mL of aqueous ethanol solution per 10 g of *ginkgo* or *Phellodendron* Bark.

3. The method of claim 1, wherein Of said *Phellodendron* Bark extract is obtained at an extraction temperature of 15 to 35° C.

4. The method of claim 1, wherein said deodorant agent comprises 0.00001 to 10 wt. % of said *Phellodendron* Bark extract in terms of solid content basis.

5. The method of claim 1, wherein said deodorant agent further comprises at least one material selected from the group consisting of finely-divided powder of a porous metal oxide, an astringent compound, a bactericidal agent, an antimicrobial agent and an antibiotic.

6. The method of claim 1, wherein said deodorant agent further comprises at least one material selected from the group consisting of an oil, a surfactant, an alcohol, a chelating agent, a pH adjuster, a preservative, a viscosity increasing agent, a colorant, a fragrance, a U.V. absorber, a whitening agent, an anti-wrinkle agent, a humectant, a sebum excretion inhibitor, an emollient, a keratin protecting agent, a pharmaceutically-active agent, an antioxidant and a solvent.

7. The method of claim 1, wherein said skin in need thereof is located on at least one site selected from the group consisting of feet, axillae, head and pubes.

8. A method for inhibiting decomposition of apolipoprotein D by a microorganism on skin comprising applying to skin in need thereof, a deodorant agent comprising *Phellodendron* Bark extract obtained with 95 v/v % or higher aqueous ethanol solution.

9. The method of claim 8, wherein said *Phellodendron* Bark extract is obtained using 70 to 100 mL of aqueous ethanol solution per 10 g of *ginkgo* or *Phellodendron* Bark.

10. The method of claim 8, wherein said *Phellodendron* Bark extract is obtained at an extraction temperature of 15 to 35° C.

11. The method of claim 8, wherein said deodorant agent comprises 0.00001 to 10 wt. % of said *Phellodendron* Bark extract in terms of solid content basis.

12. The method of claim 8, wherein said deodorant agent further comprises at least one material selected from the group consisting of finely-divided powder of a porous metal oxide, an astringent compound, a bactericidal agent, an antimicrobial agent and an antibiotic.

13. The method of claim 8, wherein said deodorant agent further comprises at least one material selected from the group consisting of an oil, a surfactant, an alcohol, a chelating agent, a pH adjuster, a preservative, a viscosity increasing agent, a colorant, a fragrance, a U.V. absorber, a whitening agent, an anti-wrinkle agent, a humectant, a sebum excretion inhibitor, an emollient, a keratin protecting agent, a pharmaceutically-active agent, an antioxidant and a solvent.

14. The method of claim 8, wherein said skin in need thereof is located on at least one site selected from the group consisting of feet, axillae, head and pubes.

* * * * *